(12) United States Patent
Xu et al.

(10) Patent No.: US 11,759,347 B2
(45) Date of Patent: Sep. 19, 2023

(54) SYSTEM AND METHOD FOR TUMOR TREATMENT

(71) Applicant: SHANGHAI JIAOTONG UNIVERSITY, Shanghai (CN)

(72) Inventors: Xuemin Xu, Shanghai (CN); Aili Zhang, Shanghai (CN); Ping Liu, Shanghai (CN); Jingfeng Bai, Shanghai (CN); Jianqi Sun, Shanghai (CN)

(73) Assignee: SHANGHAI JIAOTONG UNIVERSITY, Shanghai (CN)

( * ) Notice: Subject to any disclaimer, the term of this patent is extended or adjusted under 35 U.S.C. 154(b) by 540 days.

(21) Appl. No.: 15/324,961

(22) PCT Filed: Jul. 6, 2015

(86) PCT No.: PCT/CN2015/083412
§ 371 (c)(1),
(2) Date: May 17, 2017

(87) PCT Pub. No.: WO2016/004845
PCT Pub. Date: Jan. 14, 2016

(65) Prior Publication Data
US 2017/0252205 A1    Sep. 7, 2017

(30) Foreign Application Priority Data

Jul. 7, 2014 (CN) .......................... 201410321238.4

(51) Int. Cl.
*A61F 7/00*    (2006.01)
*A61B 18/04*   (2006.01)
(Continued)

(52) U.S. Cl.
CPC ................ *A61F 7/00* (2013.01); *A61B 18/02* (2013.01); *A61B 18/04* (2013.01); *A61F 7/007* (2013.01);
(Continued)

(58) Field of Classification Search
CPC combination set(s) only.
See application file for complete search history.

(56) References Cited

U.S. PATENT DOCUMENTS

2003/0032995 A1   2/2003   Handy et al.
2003/0082194 A1*  5/2003   Gaiger ............... C07K 14/4748
                                                     424/184.1

FOREIGN PATENT DOCUMENTS

CN    1561925 A       1/2005
CN    1709212    *   12/2005   ............... A61F 7/00
(Continued)

OTHER PUBLICATIONS

Jiaxiang Dong, Ping Liu & Dr. Lisa X. Xu. Immunologic response induced by synergistic effect of alternating cooling and heating of breast cancer. 2009. International Journal of Hyperthermia, 25:1, 25-33 (Year: 2009).*

(Continued)

*Primary Examiner* — Joseph A Stoklosa
*Assistant Examiner* — Adam J Avigan
(74) *Attorney, Agent, or Firm* — HAMRE, SCHUMANN, MUELLER & LARSON, P.C.

(57) ABSTRACT

An apparatus used for increasing the level of CD4$^+$T cells in a mammal. The mammal has a cancerous tissue. The apparatus comprises a cold treatment unit and a heat treatment unit. The cold treatment unit is used for cooling the cancerous tissue. The heat treatment unit is used for heating the cancerous tissue. A method for increasing the level of CD4$^+$ T cells in the body of a cancer patient, comprising steps for cold treatment of the cancerous tissue and for heat treatment of the cancerous tissue.

10 Claims, 3 Drawing Sheets

(51) Int. Cl.
| | |
|---|---|
| *A61B 18/02* | (2006.01) |
| *A61F 7/12* | (2006.01) |
| *A61N 5/02* | (2006.01) |
| *A61N 1/40* | (2006.01) |
| *A61N 5/06* | (2006.01) |
| *A61N 5/067* | (2006.01) |

(52) U.S. Cl.
CPC ............... *A61F 7/12* (2013.01); *A61N 5/025* (2013.01); *A61N 5/0625* (2013.01); *A61F 2007/0063* (2013.01); *A61N 1/403* (2013.01); *A61N 5/067* (2021.08); *A61N 2005/0659* (2013.01)

(56) References Cited

FOREIGN PATENT DOCUMENTS

| CN | 1709212 A | | 12/2005 | |
|---|---|---|---|---|
| CN | 1254218 C | * | 4/2006 | ............. A61B 18/02 |
| CN | 104083205 A | | 10/2014 | |

OTHER PUBLICATIONS

Maecker HT, Auffermann-Gretzinger S, Nomura LE, Liso A, Czerwinski DK, Levy R. Detection of CD4 T-cell responses to a tumor vaccine by cytokine flow cytometry. Clin Cancer Res. Mar. 2001;7(3 Suppl):902s-908s. (Year: 2001).*

Maino et al. Cytokine flow cytometry: a multiparametric approach for assessing cellular immune responses to viral antigens, Clinical Immunology. 2004, vol. 110, Issue 3, pp. 222-231 (Year: 2004).*

Dong, Jiaxiang "Immunologic Response Induced by Synergistic Effect of Alternate Cooling and Heating of Breast Cancer" Shanghai Jiao Tong University Master degree Graduation Thesis, Jul. 21, 2008 (55 pages). Cited in International Search Report.

Song et al., "The Control Method Design of Thermal Treatment System Via Fuzzy Logic", Chinese Journal of Medical Instrumentation, No. 3, vol. 36, Jun. 30, 2012, pp. 172-176. Cited in International Search Report.

Fu et al., "Development of a Cryosurgery & Radiofrequency Alternating Tumor Ablation Device", Chinese Journal of Medical Instrumentation, No. 6, vol. 32, Dec. 2008 (3 pages). Cited in International Search Report.

Martorelli et al., "Role of CD4+ cytotoxic T lymphocytes in the control of viral diseases and cancer" International Reviews of Immunology, 2010, 29 (4), pp. 371-402.

Hirschhorn-Cymerman et al. "Induction of tumoricidal function in CD4+ T cells is associated with concomitant memory and terminally differentiated phenotype", The Journal of Experimental Medicine, 2012, vol. 209, No. 11, pp. 2113-2126.

Quezada et al., "Tumor-reactive CD4+ T cells develop cytotoxic activity and eradicate large established melanoma after transfer into lymphopenic hosts", The Journal of Experimental Medicine, 2010, vol. 207, No. 3, pp. 637-650.

International Search Report and Written Opinion, International Patent Application No. PCT/CN2015/083412, dated Sep. 10, 2015 with English translation (22 pages).

* cited by examiner

SYSTEM AND METHOD FOR TUMOR TREATMENT

FIELD OF INVENTION

The present invention relates to medical engineering field and, in particular, to a system and method for regulating a level of CD4+ T cells in a tumor patient.

BACKGROUND OF INVENTION

Tumor is one of the main causes which effect human health. In theory, the tumor is not a normal portion of body, and the immune system should recognize tumor so that it suppress development of tumor. However, in fact the tumor host usually has low immunity and can not produce effective anti-tumor immunity. In recent years, the tumor immune development hypothesis about the relationship between development of tumorigenesis and the body's immune system has attracted people's attention. The hypothesis considers that the tumor cells form a stable structure of tumor immune tolerance so as to protect the tumor cells to escape immune surveillance from the body and to promote development of tumorigenesis, by reducing their own immunogenicity, down-regulating expression of co-stimulatory molecules on surface of cells, releasing a large number of immunosuppressive factors, and gathering a variety of immunosuppressive cells. Also, it is the immune tolerance induced by the immune that leads to poor treatment of cancer. Therefore, the study on the mechanism of tumor immune tolerance and how to break the immune tolerance of cancer has become focus of attention. Most malignant tumors can cause immunosuppression activity with different extents, so that the tumor can escape from surveillance and attack of the body immunity and can promote development of tumor. However, these treatment methods can not effectively alleviate the micro-environment of immunosuppression activity or effectively stimulate the body to produce systemic anti-tumor immune response so that development of cancer metastasis can not be completely inhibited and the treatment effect is very limited. Clinically, after breast cancer is treated, there are still a large portion of patients facing death. The ideal goal of new means of cancer treatment should fully relieve micro-environment of immuno-suppressive activity, and fully stimulate the body to produce anti-tumor immune response.

The immune organs of humans can be divided into central immune organs and peripheral immune organs. The central immune organs consist of bone marrow and thymus, while the peripheral immune organs comprise spleen, lymph nodes and mucosa-associated lymphoid tissue. The peripheral immune tolerance to tumor antigens is a major obstacle for anti-tumor immunity effect. In general, lymph nodes are considered as a main site where tumor antigens are presented to T cells and cause peripheral immune tolerance. However, the accumulation of immature myeloid cells in lymph nodes is extremely limited. The previous researches have shown that the spleen as a main peripheral immune organ, experiences proliferation of bone marrow cells during the development of tumor, and plays a key role in immune tolerance induced by tumor. When analyzing spleen immune environment, it has found that $CD4^+$ and $CD8^+$ T cells are the most important anti-tumor cells immune mediator. Thus, the skilled in the art have endeavored to develop a method that can improve level of $CD4^+$ and/or $CD8^+$ T cells in tumor patients.

Breast cancer is the most common malignant tumor in women, and the tumor metastasis is the main cause of death in cancer patients. At present, the tumor treatment such as surgery, radiotherapy and chemotherapy, does not have any ideal effect, and can cause significant side effects. Especially for metastatic tumors, there is almost no effective treatment. When compared with the normal blood vessels, because of the abnormal proliferation of blood vessel of malignant tumor, the blood vessel wall is weak, the degree of differentiation is low, and the smooth muscle and complete basement membrane structure is missing. There are large gaps among the endothelial cells, and the permeability is strong so that it is easy for tumor cells to penetrate the blood vessel wall and form distal metastasis focuses. In view of the current status of breast cancer treatment, it is urgent to develop a novel cancer treatment method.

SUMMARY OF INVENTION

The aim of the invention is to provide a method for improving anti-tumor immune response of a cancer-bearing mammal and a system for implementing the method.

According to the first aspect of the present invention, it provides a device for increasing a level of $CD4^+$ T cells in a mammal, wherein the mammal has a cancerous tissue, and the device comprises: a cold treatment unit and a heat treatment unit, wherein the cold treatment unit is used to cool the cancerous tissue; and the heat treatment unit is used to heat the cancerous tissue.

In another preferred embodiment, the cold treatment unit comprises a cold source which comprises liquid nitrogen, liquid oxygen or liquid nitrous oxide.

In another preferred embodiment, the cold treatment unit cools the cancerous tissue with liquid nitrogen, liquid oxygen or liquid nitrous oxide.

In another preferred embodiment, the cold treatment unit is cooled by low temperature argon or liquid argon obtained from a throttling device.

In another preferred embodiment, the heat treatment unit heats the cancerous tissue by using irradiation of radio frequency, microwave, infrared radiation or laser radiation, or electric heating. In another preferred embodiment, the device further comprises a temperature monitoring unit for monitoring temperature of the cancerous tissue.

In another preferred embodiment, the device further comprises a $CD4^+$ T cell level monitoring unit for detecting the level of $CD4^+$ T cells in the mammal.

In another preferred embodiment, the device further comprises a contact head which has a contact surface for closely fitting with the cancerous tissue, and the cold source cools the cancerous tissue with the contact head, and/or the heat source heats the cancerous tissue with the contact head.

In another preferred embodiment, the contact surface has an area of 0.1 to 10 $cm^2$; preferably, the contact surface has an area of 0.25 to 5 $cm^2$.

In another preferred embodiment, the contact surface is a circular plane or the contact surface is a curved surface of a spherical or nearly spherical surface.

According to the second aspect of the present invention, it provides a method for increasing a level of $CD4^+$ T cells in a mammal, wherein the mammal has a cancerous tissue, and the method comprises the following steps:

(1) cold treatment: treating at least one or more cancerous tissues of the mammal with cold treatment, wherein the cold treatment comprises lowering the treated cancerous tissue to a temperature of −10° C. or below and maintaining the temperature for 2-20 minutes;

(2) rewarming treatment: warming the cold treated cancerous tissue to a temperature of 5-25° C.; and (3) heat treatment: treating the rewarmed cancerous tissue treated in the previous step with heat treatment, wherein the heat treatment comprises raising temperature of the cancerous tissue to 45-60° C. and maintaining for 2-20 minutes.

In another preferred embodiment, the method further comprises a step of:

(4) Repeating steps (1) to (3) one or more times.

In another preferred embodiment, the cancerous tissue has a volume of less than 1000 cm$^3$; preferably, the cancerous tissue has a volume of less than 500 cm$^3$; and more preferably, the cancerous tissue has a volume of 0.1 cm$^3$ to 100 cm$^3$.

In another preferred embodiment, the cancerous tissue comprises: tumor, tissue invaded by cancer cells, tumor metastasis focus, and blood of tumor patient.

In another preferred embodiment, the cancerous tissue is a superficial cancerous tissue or a cancerous tissue located in the body.

In another preferred embodiment, in steps of cold treatment or heat treatment, the treatment is operated with non-invasive or minimal invasive method.

In another preferred embodiment, the method further comprises monitoring temperature of the cancerous tissue in steps (1) to (3).

In another preferred embodiment, the monitoring temperature of the cancerous tissue includes non-invasive temperature monitoring, such as temperature detection via infrared image analysis, nuclear magnetic resonance temperature detection, and ultrasonic temperature detection.

In another preferred embodiment, in step (1) of cold treatment, the cold treatment is carried out by contacting the cold source or its transfer device with the skin.

In another preferred embodiment, in step (3) of heat treatment, the heat treatment is carried out by contacting the heat source or its transfer device with the skin.

In another preferred embodiment, the transfer device includes a contact head which comprises a contact surface for closely fitting with the cancerous tissue. The cold source cools the cancerous tissue with the contact head, and/or the heat source heats the cancerous tissue with the contact head.

In another preferred embodiment, the cancerous tissue carried by the mammal comprises metastatic cancerous tissue.

In another preferred embodiment, the tumor comprises malignant solid tumor, blood tumor and benign tumors.

In another preferred embodiment, the cancerous tissue is a superficial cancerous tissue.

In another preferred embodiment, in step (1), the cancerous tissue is cooled to a temperature of −10° C. to −30° C. which is maintained for 5 minutes to 20 minutes during the cold treatment.

In another preferred embodiment, in step (1), the cancerous tissue is cooled to a temperature of −15° C. to −25° C. during the cold treatment. Preferably, the cancerous tissue is cooled to a temperature of −18° C. to −20° C.

In another preferred embodiment, in step (1), the low temperature is maintained for a period of 10 min to 25 min; preferably, the low temperature is maintained for a period of 15 min to 20 min.

In another preferred embodiment, in step (3), the cancerous tissue is heated to a temperature of 45° C. to 55° C. during the heat treatment. Preferably, the cancerous tissue is heated to a temperature of 50° C. to 55° C.

In another preferred embodiment, in step (3), the high temperature is maintained for a period of 5 min to 25 min. Preferably, the high temperature is maintained for a period of 10 min to 20 min.

In another preferred embodiment, in step (3), the cancerous tissue is heated to a temperature of 50° C. to 55° C. which is maintained 5 minutes to 15 minutes during the heat treatment.

In another preferred embodiment, the method further comprises: measuring a level of CD4$^+$ T cells after the heat treatment in step (3).

In another preferred embodiment, the method further comprises: measuring a level of CD8$^+$ T cells after the heat treatment in step (3).

In another preferred embodiment, the method further comprises: detecting and evaluating the cancerous tissue, in particular the metastasis focus, after the heat treatment in step (3).

According to the third aspect of the present invention, it provides a method for treating tumor which comprises using the method of the second aspect of the present invention to increase a level of CD4$^+$ T cells in a tumor patient.

According to the fourth aspect of the present invention, it provides a method for releasing (or presenting) immunogen of a cancerous tissue, which comprises:

(1) cold treatment: treating the cancerous tissues with cold treatment, wherein the cold treatment comprises lowering the treated cancerous tissue to a temperature of −10° C. or below and maintaining the temperature for 2-20 minutes;

(2) rewarming treatment: warming the cold treated cancerous tissue of the previous step to a temperature of 5-25° C.; and (3) heat treatment: treating the rewarmed cancerous tissue treated in the previous step with heat treatment, wherein the heat treatment comprises raising the cancerous tissue to a temperature of 45-60° C. and maintaining for 2-20 minutes.

In another preferred embodiment, the method further comprises a step of:

(4) Repeating steps (1) to (3) one or more times.

In another preferred embodiment, the cancerous tissue is an isolated cancerous tissue.

In another preferred embodiment, the method of releasing the immunogen of cancerous tissue is used for non-diagnostic or non-therapeutic purpose.

In another preferred embodiment, the cancerous tissue has a volume of less than 1000 cm$^3$; preferably, the cancerous tissue has a volume of less than 500 cm$^3$; and more preferably, the cancerous tissue has a volume of 0.1 cm$^3$ to 100 cm$^3$. Alternatively, in other embodiments, the cancerous tissue has a volume of greater than 1000 cm$^3$.

In another preferred embodiment, the cancerous tissue comprises: tumor, tissue invaded by cancer cells, tumor metastasis focus, and blood of tumor patient.

In another preferred embodiment, the method further comprises monitoring temperature of the cancerous tissue in steps (1) to (3).

In another preferred embodiment, the monitoring temperature of the cancerous tissue includes non-invasive temperature monitoring, such as temperature detection via infrared image analysis, nuclear magnetic resonance temperature detection, and ultrasonic temperature detection.

In another preferred embodiment, in step (1) of cold treatment, the cold treatment is carried out by contacting the cold source or its transfer device with the skin.

In another preferred embodiment, in step (3) of heat treatment, the heat treatment is carried out by contacting the heat source or its transfer device with the skin.

In another preferred embodiment, the transfer device includes a contact head which comprises a contact surface for closely fitting with the cancerous tissue. The cold source cools the cancerous tissue with the contact head, and/or the heat source heats the cancerous tissue with the contact head.

In another preferred embodiment, the tumors comprises malignant solid tumor, blood tumor and benign tumor.

In another preferred embodiment, in step (1), the cancerous tissue is cooled to a temperature of −10° C. to −30° C. Which is maintained for 5 minutes to 20 minutes during the cold treatment.

In another preferred embodiment, in step (1), the cancerous tissue is cooled to a temperature of −15° C. to −25° C. during the cold treatment. Preferably, the cancerous tissue is cooled to a temperature of −18° C. to −20° C.

In another preferred embodiment, in step (1), the low temperature is maintained for a period of 10 to 25 minutes; preferably, the low temperature is maintained for a period of 15 to 20 minutes.

In another preferred embodiment, in step (3), the cancerous tissue is heated to a temperature of 45° C. to 55° C. during the heat treatment. Preferably, the cancerous tissue is heated to a temperature of 50° C. to 55° C.

In another preferred embodiment, in step (3), the high temperature is maintained for a period of 5 to 25 minutes. Preferably, the high temperature is maintained for a period of 10 to 20 minutes.

In another preferred embodiment, in step (3), the cancerous tissue is heated to a temperature of 50° C. to 55° C. and such temperature is maintained for 5 to 15 minutes during the heat treatment.

It should be understood that, within the scope of the present invention, the technical features specifically described above and below (such as in the Examples) can be combined with each other, thereby constituting a new or preferred technical solution which needs not be described one by one.

DETAILED DESCRIPTION OF THE INVENTION

Figure 1:
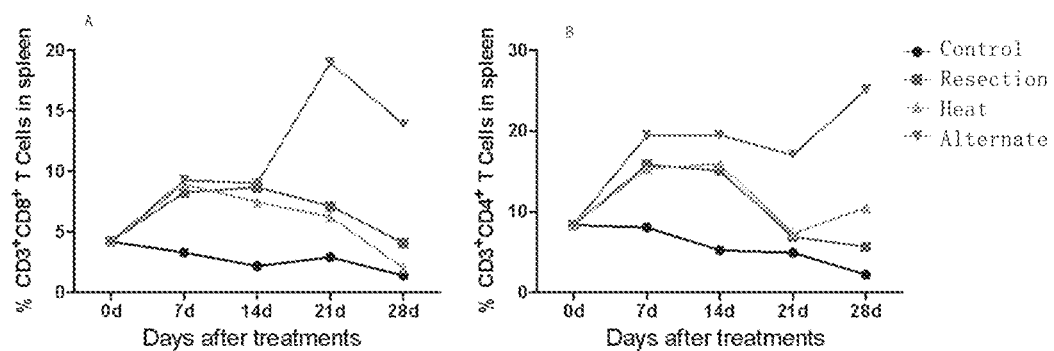
FIG. 1 shows changes of immune cells in spleen induced in different treatment groups, wherein Figure A shows changes of level of $CD8^+$ T cells in spleen; and Figure B shows changes of level of $CD4^+$ T cells in spleen.
Figure 2:
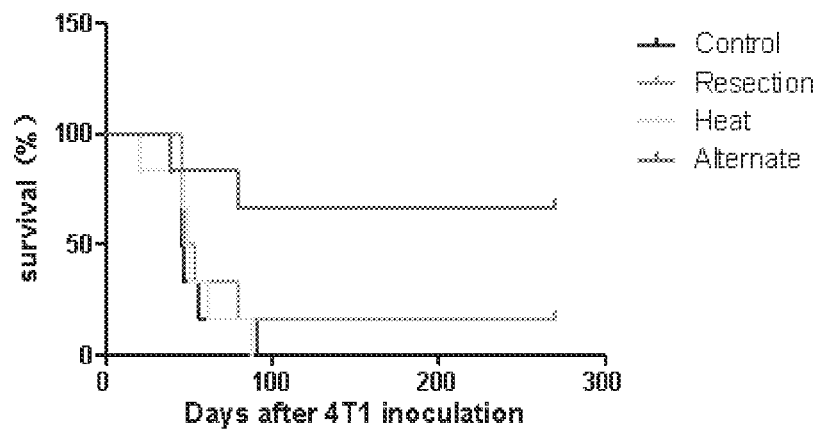
FIG. 2 shows the overall survival percentage and survival time in different groups of mice (6 mice in each group).

Through extensive and intensive studies, the inventors of the present invention have obtained a method for improving level of $CD4^+$ T cells in tumor patients. The experimental results have shown that the treatment of cancerous tissue by alternate cold and heat can significantly improve level of $CD4^+$ T cells in tumor patients. The present invention also provides a system useful in said method.

Treatment System or Device:

In a preferred embodiment, the device of the present invention for improving level of $CD4^+$ T cells of mammals comprises: a cold treatment unit and a heat treatment unit, wherein the cold treatment unit is used to cool the cancerous tissue; and the heat treatment unit is used to heat the cancerous tissue. The cold treatment unit comprises a cold source which can be liquid nitrogen, liquid oxygen or liquid nitrous oxide. The cold treatment unit cools the cancerous tissue with liquid nitrogen, liquid oxygen or liquid nitrous oxide. The heat treatment unit heats the cancerous tissue by using irradiation of radio frequency, microwave, infrared radiation or laser radiation, electric heating or the like.

In another preferred embodiment, the device further includes a temperature monitoring unit for monitoring temperature of the cancerous tissue.

In another preferred embodiment, the device further comprises a $CD4^+$ T cell level monitoring unit for detecting level of $CD4^+$ T cells in mammals.

In another preferred embodiment, the device further comprises a contact head which comprises a contact surface for closely fitting the cancerous tissue, and the cold source cools the cancerous tissue with the contact head, and/or the heat source heats the cancerous tissue with the contact head.

In another preferred embodiment, the contact surface is a circular plane or the contact surface is a curved surface of a spherical or nearly spherical surface.

In another preferred embodiment, the means for conduct the cold treatment (low temperature treatment) of cancerous tissue in the present invention includes:

(1) using the transportation and accurate control of flow of liquid nitrogen, liquid oxygen, or liquid nitrous oxide so as to obtain the desired temperature of the invention;

(2) using throttle nozzle design and throttle effect of argon so as to obtain the desired temperature of the invention.

In preferred embodiments, the means for conducting heat treatment (heating) of cancerous tissue in the present invention includes: using irradiation of radio frequency, microwave, infrared radiation or laser radiation, or direct electric heating so as to obtain the desired temperature of the invention.

In a preferred embodiment of the present invention, the device used as the cold and heat alternating treatment system is described in Chinese Patent application of CN2005100343.8 and CN200410017864.0.

The main advantages of the present invention includes:

(1) In the present invention, a method for effectively improving level of $CD4^+$ T cells in tumor patients is disclosed for the first time. The experimental results have shown that treating tumor-bearing mice by the method of the invention can significantly improve level of $CD4^+$ T cells in mice;

(2) Treating the tumor-bearing mice by the method of the invention can significantly improve the survival percentage.

(3) Treating the tumor-bearing mice by the method of the invention can significantly reduce metastasis of tumor cells in tumor-bearing mice.

The invention is further illustrated by the following examples. It should be appreciated that these examples are only intended to illustrate the invention, but not to limit the scope of the invention. Unless indicated otherwise, all percentage and parts are calculated by weight.

EXAMPLES

1. Materials and Methods

1.1 Animals, Cell Lines and Main Reagents

SPF Balb/c female mice aged 6-8 weeks (Shanghai Slac Animal Center) are kept in a separate ventilation box cage. An artificially control light of 12 hrs day light and 1.2 hrs night light is used. The mice can freely take feed sterilized with $^{60}Co$ radiation and water sterilized with high temperature. Mouse 4T1 breast cancer cells (obtained from Shanghai First People's Hospital. In other embodiments, other breast cancer cells such as T47D cell line can be used.) are cultured in RPMI 1640 medium (Hyclone Co., USA) supplemented with 10% newborn fetal bovine serum (HangZhou Sijiging Co., Ltd.) and double antibiotics (100 U/mL penicillin and 100 g/mL streptomycin) (Shanghai Biotechnology Engineering Co., Ltd.). Ultra-fine precipitation of barium sulfate particles is purchased from Shanghai Zewen Trade Co., Ltd. FITC-labeled CD4 and PE-labeled CD8 for flow cytometry and immunofluorescence are purchased from Biolegend. Hematoxylin and eosin solution are purchased from Shanghai Hongqiao Le Xiang Medical Reagent Co., Ltd.

1.2 Establishment of 4T1 Breast Cancer Model and Determination of Tumor Size The 4T1 mouse breast cancer cell used in this study is capable of metastasis to lungs, liver, bone marrow and brain via hematogenous pathways, and is a model of highly metastatic breast cancer. $1\times10^6$ U/0.1 mL of 4T1 cells suspension was prepared and placed on ice. Animals were anesthetized by intraperitoneal injection of 0.016 g/mL pentobarbital sodium in a dose of 0.5 mL/100 g mice, and 0.1 mL cell suspension was subcutaneously injected into the back of mice. 21 days after tumor inoculation, the tumor volume was measured with a vernier caliper, and calculated according to the following formula: V ($cm^3$)=p×long axis of tumor (cm)×short axis of tumor (cm)×tumor height (cm)/6. The tumor-bearing mice were randomly divided into control group, surgical resection treatment group, heat treatment group, and heat and cold combination treatment group. In 4T1 mouse breast cancer animal model established by the inventors, the mice were found to have micro-metastasis in the liver or the like 21 days after inoculation of tumor cells by using PET/CT scans and F18-labeling in vivo. Therefore, the present inventors selected 21 days after tumor inoculation as a time window for treatment.

1.3 Alternate Heat and Cold Treatment

1.3.1 Experimental Scheme

The control group (the tumor-bearing mice, Control, referred as C), the surgical resection treatment group (Resection treatment, referred as R), the heat treatment group (Heat treatment, referred as H) and heat and cold combination treatment group (Alternate cooling and heating treatment, referred to as A). The research was as follows: (1) 21 days after inoculation, the mice were randomly divided into four groups and treated respectively: control group (C), surgical resection treatment group (R), heat treatment group (H) and heat and cold combination treatment group (A). After treatment, six mice from each group were selected to observe long-term therapeutic effect. In addition, three mice from each group were selected, and the lungs of the mice were taken 28 days after the treatment to detect lung metastasis of mice after treatment. (2) At 0 day before the treatment (that is 21 days after inoculation) and 7 days, 14 days, 21 days and 28 days after treatment, the mice were sacrificed, and the spleen and peripheral blood of mice in each group were taken to analyze the immunized cells. In addition, in order to further observe changes in immune environment of the metastatic lungs, 14 days after treatment, additional 3-5 mice from each group were taken to conduct lung analysis.

1.3.2 Alternate Heat and Cold Treatment System

A device for improving level of $CD4^+$ T cells in mammals in the present embodiment comprises: a cold treatment unit and a heat treatment unit; the cold treatment unit is used to cool the cancerous tissue; and the heat treatment unit is used to heat the cancerous tissue. The cold treatment unit comprises a cold source liquid nitrogen, and the liquid nitrogen is used to cool the cancerous tissue. The heat treatment unit heats the cancerous tissue by irradiation of radio frequency. The device includes a contact head which comprises a contact surface for closely fitting the cancerous tissue. The cold source cools the cancerous tissue with the contact head, and the heat source heats the cancerous tissue with the contact head. The contact surface is a circular plane which is particularly suitable for model of superficial tumor used in this experiment.

1.3.3 Experimental Process

The mice were treated 21 days after tumor inoculation. The tumor volume before treatment was measured, and the mice with average tumor volume of less than 0.2 $cm^3$ were selected as treatment subject. Before treatment, the mice were randomly divided into four groups and treated respectively: control group, surgical resection treatment group, heat treatment group, and heat and cold combination treatment group. First, mice to be treated were anesthetized, and sterilized with alcohol and iodine tincture at the tumor site.

During treatment, the probe was placed on surface of tumor and a thermocouple for temperature measurement was inserted into base of tumor. During heating treatment, radiofrequency was used to heat the tumor so that the tumor was heated to a temperature of 50° C. (the temperature which was measured with the thermocouple) and it was maintained for 15 minutes. Alternate heat and cold treatment was divided into three processes: (1) cold treatment wherein tumor was lowered to a temperature of −20° C. by means of liquid nitrogen cooling and maintained at such temperature for 5 minutes; (2) rewarming wherein the tumor after cold treatment was naturally rewarmed to about 10° C.; (3) heat treatment wherein at the end of rewarming process, the temperature of was raised to 50° C. by the radiofrequency heat and such temperature was maintained for 10 mins

1.3.4 Evaluation on Efficacy of Cold and Heat Treatment

After treatment, the survival status of mice was observed comprehensively. This part of study mainly includes: observation of in situ tumor growth in control group, in situ tumor ablation and recurrence in treatment group and metastasis of mice in each group (daily), records of change of body weight of mice before and after treatment (twice a week), statistics of long-term survival percentage and survival time of mice and so on. These indicators could effectively reflect survival of mice, wherein statistics of survival percentage and survival time are the most important indicators for evaluation of treatment

1.3.5 Lung Analysis Based on H&E Staining

At 28 days after treatment, the mice were sacrificed. After perfusion of 4% formaldehyde into lungs though the weasand, the lungs were removed, and placed in formalin for 48 hours for fixation. After the lungs were embedded with paraffin, the specimen was cut into 8 microns of paraffin slices by using a paraffin slicing machine and the slices were stored at room temperature. The slices were dewaxed with xylene and a gradient from alcohol (100% −90% −80% −70%) to water was used. The paraffin slices was stained with hematoxylin-eosin (H&E), incubated in hematoxylin solution for about 10 minutes, washed with tap water for about 20-30 mins. A gradient of alcohol (70% –80% –90% –100%) was used for dehydration. The slices was fixed with xylene for two hours, sealed with neutral gum and air dried. After completion of staining, the slide was placed under a microscope to observe lung metastasis. The regions of interest were observed, photographed and recorded.

1.3.6 Flow Cytometry Analysis

At 0 day before the treatment (i.e., 21 days after inoculation) and 7 days, 14 days, 21 days and 28 days after treatment, mice were sacrificed, and spleen and peripheral blood of mice in each group were taken to analyze immunized cells. The spleen of mice was taken and placed on a 70 micrometer nylon cell filter, milled with a 5 ml syringe and rinsed with DMEM into a 50 ml centrifuge tube. After centrifuging at 2000 rpm for 10 minutes, the supernatant was discarded, and 2 ml erythrocyte lysate was added and blown evenly, at room temperature for 5 minutes. Add PBS and after dilution as much as possible abandon the supernatant, then get the spleen white blood cells. After resuscitation, add 1 µl corresponding fluorescent antibody (label the cell surface molecules to detect the specific cell populations, specific labeling in table 7) and incubate for 30 minutes at 4° C. After washed by PBS and then resuspended, carry into the flow tube on the machine to detect. In addition, the function of T cells was further identified in this experiment, and labeled $CD4^+$ T cells and $CD8^+$ T cells were sorted by flow cytometry.

1.3.7 Data Statistics

The statistics and analysis of all experimental data in experiments were performed by using Graph pad Prism software, and Student's t test was used to analyze the difference between groups. The results were shown as mean±standard deviation. Image Pro Plus software was used to analyze area data of lungs metastasis. The FlowJo software was used to process image of flow cytometry.

2 Results 2.1 Change of Level of $CD4^+$ T Cells in Spleen

It was found in the study that the anti-tumor immune cells ($CD4^+/CD8^+$ T cells) in spleen in only-heat-treatment group and resection group were similar to those in alternate cold and heat treatment group within 14 days after treatment. All showed a tendency of increase. 14 days after treatment, $CD4^+/CD8^+$ T cells began to decrease gradually in spleen in only-heat-treatment group and resuscitation group, and at day 28, $CD4^+/CD8+$ T cells in only-heat-treatment group and surgery resection group decreased almost to the same level as that in control group. The levels of $CD4^+/CD8^+$ T cells were significantly increased in alternate heat and heat treatment group within 21 days, and the level of $CD8^+$ T cells began to decrease after 21 days, but the level of $CD4^+$ T cells was still significantly increased. The results of experiment are shown in FIG. 1. FIG. 1 shows change of immune cells in spleen induced in different treatment groups.

2.2 Cold and Heat Treatment Improves Survival Percentage of Mice

Figure 6:
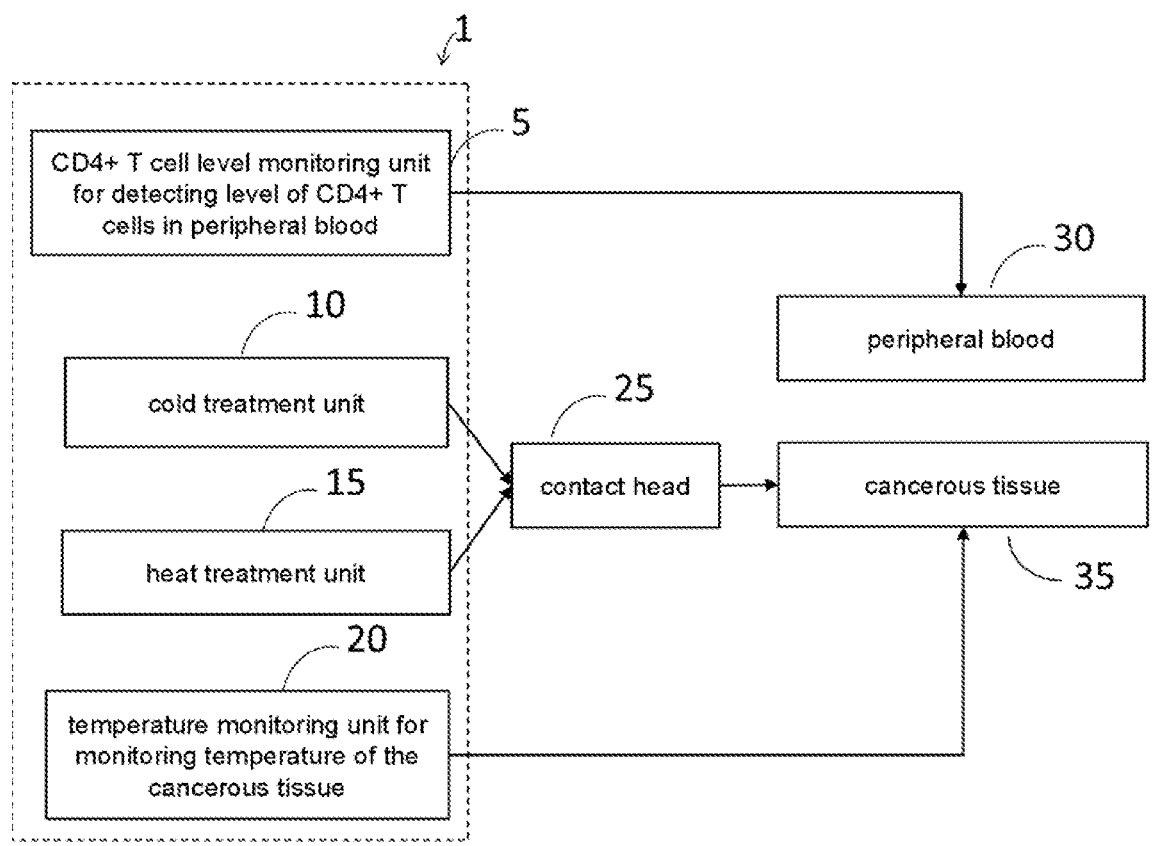
FIG. 6 illustrates a treatment device for increasing a level of $CD4^+$ T cells in a mammal having a tumor, in accordance with an embodiment.

The mice were observed for 3 months after treatment, and there were 6 mice in each group. After alternate cold and heat treatment, 4 mice of them had a good living condition, and almost all of mice died in control group, only-heat-treatment group and surgery resection group. Therefore, alternate cold and heat treatment of tumor could greatly improve survival percentage of mice, and achieve a good therapeutic effect. FIG. 6 shows the overall survival percentage and survival time of mice in different groups (6 mice in each group).

2.3 Cold and Heat Treatment Inhibits Tumor Metastasis

Figure 3:
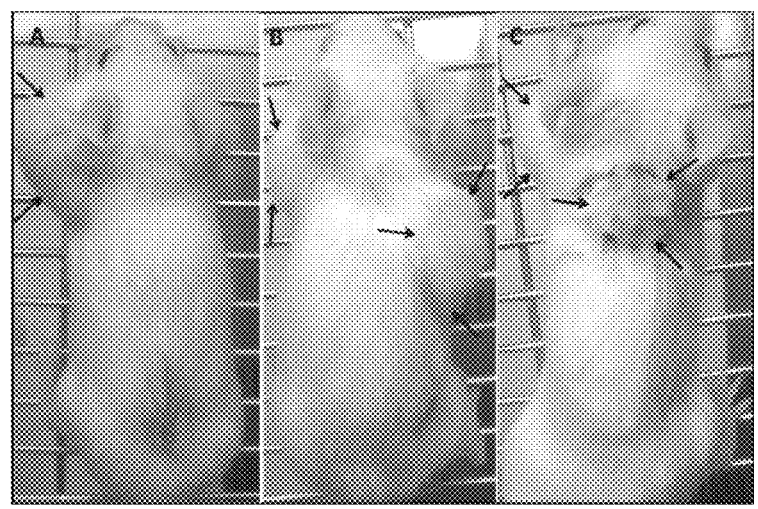
FIG. 3 shows tumor metastasis on surface of mice three weeks after treatment, wherein Figure A shows the treatment group of surgical resection, Figure B shows treatment group only with cold treatment, and Figure C shows the treatment group with only heat treatment.
Figure 4:
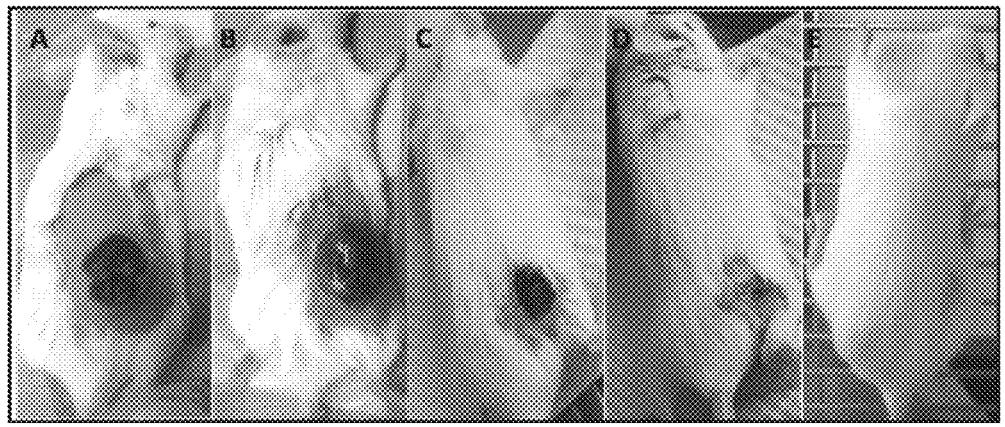
FIG. 4 shows the status of the mice 6 weeks after cold and heat treatment. Figure A shows the mice before the treatment; Figure B shows the mice after the treatment; Figure C shows the mice 1 week after treatment; Figure D shows the mice 3 weeks after treatment; and Figure E shows the mice 6 weeks after treatment.

The mice in surgery resection group, only-cold-treatment group and only-heat-treatment group began to appear metastasis in their body surface three weeks after treatment (see FIG. 3). After alternate cold and heat treatment, tumor began to subside, to scab, and even to ablation (as shown in FIG. 4). Especially after 6 weeks of alternate cold and heat treatment, the in situ tumors in tumor-bearing mice were completely ablated and there was no metastasis tumor on their body surface, and the mice lived well. FIG. 3 shows tumor metastasis of mice three weeks after treatment wherein (A) is the surgical resection treatment group, (B) is the only-cold-treatment group, and (C) is the only-heat-treatment group. FIG. 4 shows the mice within 6 weeks after alternate cold and heat treatment wherein (A) is before treatment; (B) is after treatment; (C) is 1 week after treatment; (D) is 3 weeks after treatment; and (E) is 6 weeks after treatment.

Figure 5:
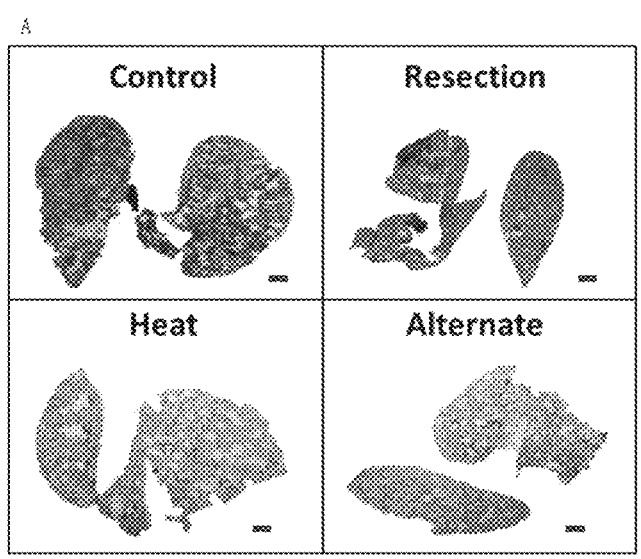
FIG. 5 shows lung metastases detected via H&E staining 28 days after treatment. Figure A shows microscopic observation via H&E staining; and Figure B shows lung metastases in each treatment group.
Figure 5:
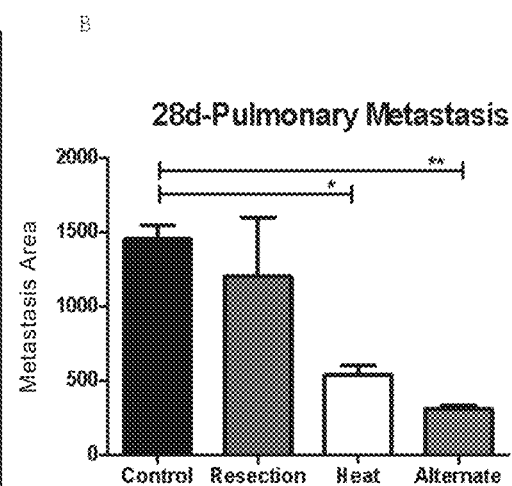

Then the paraffin sections of lung of mice in different treatment groups were stained with hematoxylin and observed. The lung metastasis was compared between the control group and different treatment groups (see FIG. 5). It was found in the study that in the surgical resection group, there was abnormal lung structure and significant tumor metastasis, and there was no significant difference of tumor metastasis area when compared with the control group. There were some small metastatic nodules in the only-heat-treatment group and lung tissue structure was relatively normal, and the area of lung tumor metastasis was significantly decreased. In the alternate cold and heat treatment group, some small metastatic nodules were observed, the lung tissue structure was relatively normal, and the area of tumor metastasis was decreased most significantly. FIG. 5 shows lung metastases of tumor 28 days after treatment, and it can be seen that the metastatic area in the alternate cold and heat treatment group is significantly lower than those in other groups.

Referring to FIG. 6, FIG. 6 illustrates a treatment device 1 for increasing a level of $CD4^+$T cells in a mammal having a tumor in accordance with an embodiment. The treatment device 1 can include a $CD4^+$T cell level monitor unit 5 for detecting the level of $CD4^+$T cells in peripheral blood 30, a cold treatment unit 10, a heat treatment unit 15, a contact head 25, and a temperature monitoring unit for monitoring the temperature of the cancerous tissue 35.

3. CONCLUSION AND DISCUSSION

In this study, 4T1 breast cancer was used as a model to study efficacy of alternate cold and heat treatment of local tumor on $CD4^+$ and $CD8^+$ T cells in peripheral blood and spleen. The results surprisingly showed that after alternate cold and heat treatment of tumor tissue, $CD4^+$ and $CD8^+$ T cells in mice were significantly increased within 21 days, but after 21 days, the level of $CD8^+$ T cells in mice began to decrease, while the level of $CD4^+$ T cells began to increase significantly with the decrease of $CD8^+$ T cells.

Studies have shown that $CD4^+$ T cells also have cytotoxic effects[1]. In specific cases, such as when lymphopenia cells decrease, $CD4^+$ T cells can obtain an ability to directly kill cells[2, 3]. In $CD4^+$ T cells, there are mainly Fas pathway and another INF-related apoptosis-inducing ligand pathway to mediate their cytotoxic effects[1]. In this study, it has been found that, compared with $CD8^+$ T cells, $CD4^+$ T cells in spleen and blood are more significantly increased after alternate cold and heat treatment, and also can secrete cytotoxic cytokines such as IFN-γ, so they have strong cytotoxic effects. Further, in the peripheral blood, 14 days after treatment, when compared with other groups in which $CD4^+$ T cells decreased significantly, the same cells in alternate cold and heat group maintained a high level for a long period. These experimental data suggest that $CD4^+$ T cells play a more important role. The present invention can induce $CD4^+$ T cells by cold and heat treatment, enhance anti-tumor immunity in the body, significantly reduce mortality of tumor-bearing mice, and extend survival time of mice in the experiment.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be in the scope of the invention defined by the appended claims of the application.

REFERENCES

[1]. Martorelli, D., Muraro, E., Merlo, A., et al., Role of $CD4^+$ cytotoxic T lymphocytes in the control of viral diseases and cancer [J]. International reviews of immunology, 2010, 29 (4), pp 371-402.
[2]. Hirschhorn-Cymerman, D., Budhu, S., Kitano, S., et al., Induction of tumoricidal function in $CD4^+$ T cells is associated with concomitant memory and terminally differentiated phenotype [J]. The Journal of experimental medicine, 2012, 209 (11), pp 2113-2126.
[3]. Quezada, S. A., Simpson, T. R., Peggs, K. S., et al., Tumor-reactive T cells develop cytotoxic activity and eradicate large established melanoma after transfer into lymphopenic hosts [J]. The Journal of experimental medicine, 2010, 207 (3), pp 637-650.

The invention claimed is:

1. A method for increasing a level of CD4+ T cells in peripheral blood in a mammal, wherein the mammal has a cancerous tissue, and the method comprises the following steps:
   (1) cold treatment: treating at least one or more cancerous tissues of the mammal with a cold treatment to obtain a cold-treated cancerous tissue, wherein the cold treatment comprises cooling the cancerous tissue to a temperature of $-10°$ C. or below and maintaining the temperature for 2-20 minutes;
   (2) rewarming treatment: naturally warming the cold-treated cancerous tissue to a temperature of 5-25° C. to obtain a rewarmed cancerous tissue;
   (3) heat treatment: treating the rewarmed cancerous tissue with heat treatment via irradiation of radio frequency or microwave, wherein the heat treatment comprises heating the rewarmed cancerous tissue to a temperature of 45-60° C. and maintaining the temperature for 2-20 minutes; and
   (4) measuring a level of the CD4+T cells in spleen and the peripheral blood on day 0, day 7, day 14, day 21, and day 28 after step (3) via a flow cytometry wherein a fluorescent antibody is used to label cell surface molecules to detect the specific CD4+T cell population;
   wherein the CD4+T cells secrete a cytotoxic cytokine IFN-γ and have a strong cytotoxic effect;
   wherein the cancerous tissue is a superficial cancerous tissue;
   the method further comprises monitoring temperature of the cancerous tissue in steps (1) to (3), wherein the monitoring temperature of the cancerous tissue includes non-invasive temperature monitoring;
   wherein the cold treatment and the heat treatment are operated with a non-invasive method;
   wherein in step (1) of cold treatment, the cold treatment is carried out by contacting the skin with a transfer device;
   wherein in step (3) of heat treatment, the heat treatment is carried out by contacting the skin with the transfer device;
   wherein the transfer device includes a contact head which comprises a contact surface for closely contacting a surface of the cancerous tissue, wherein a cold source cools the cancerous tissue with the contact head, and a heat source heats the cancerous tissue with the contact head;
   wherein the contact surface is a circular plane or a spherical surface; and
   the contact surface of the contact head has an area of 0.25 $cm^2$ to 10 $cm^2$.

2. The method according to claim 1, wherein the cancerous tissue comprises a tumor, a tissue invaded by cancer cells, and/or a tumor metastasis focus.

3. The method according to claim 1, wherein the non-invasive temperature monitoring is temperature detection via infrared image analysis, nuclear magnetic resonance temperature detection, or ultrasonic temperature detection.

4. The method according to claim 1, wherein the method further comprises a step of: repeating steps (1) to (3) one or more times.

5. A method for releasing immunogen of a cancerous tissue of a mammal comprising:
   (1) cold treatment: treating the cancerous tissues to obtain a cold-treated cancerous tissue, wherein the treating comprises cooling the cancerous tissue to a temperature of $-10°$ C. or below and maintaining the temperature for 2-20 minutes;
   (2) rewarming treatment: naturally warming the cold-treated cancerous tissue to a temperature of 5-25° C. to obtain a rewarmed cancerous tissue;
   (3) heat treatment: treating the rewarmed cancerous tissue via irradiation of radio frequency or microwave, wherein the heat treatment comprises heating the rewarmed cancerous tissue to a temperature of 45-60° C. and maintaining the temperature for 2-20 minutes, and
   (4) measuring a level of CD4+T cells in spleen and peripheral blood on day 0, day 7, day 14, day 21, and day 28 after step (3) via flow cytometry wherein a fluorescent antibody is used to label cell surface molecules to detect the specific CD4+T cell population;
   the method further comprises monitoring temperature of the cancerous tissue in steps (1) to (3), wherein the monitoring temperature of the cancerous tissue includes non-invasive temperature monitoring:
   wherein the cold treatment and the heat treatment are operated with a non-invasive method;
   wherein the CD4+T cells secrete cytotoxic cytokine IFN-γ and have a strong cytotoxic effect;
   wherein the cold treatment in step (1) and the heat treatment in step (3) are conducted with a system comprising a treatment device;
   wherein the treatment device comprises a cold treatment unit, a heat treatment unit, and a contact head;
   wherein the cold treatment unit comprises a cold source;
   wherein the heat treatment unit comprises a heat source;

wherein the contact head comprises a contact surface for closely contacting a surface of the cancerous tissue;

wherein the cold source cools the cancerous tissue by the contact head, and the heat source heats the cancerous tissue by the contact head;

wherein the contact surface is a circular plane or a spherical surface; and wherein the contact surface of the contact head has an area of 0.25 to 10 cm$^2$.

6. The method according to claim 5, wherein the cancerous tissue has a volume of 0.1 cm$^3$ to 100 cm$^3$.

7. The method according to claim 5, wherein in step (1), the cancerous tissue is cooled to a temperature of −18° C. to −20° C.

8. The method according to claim 5, wherein in step (1), the temperature is maintained for a period of 15 to 20 minutes.

9. The method according to claim 5, wherein in step (3), the rewarmed cancerous tissue is heated to a temperature of 45° C. to 55° C. during the heat treatment.

10. The method according to claim 5, wherein in step (3), the rewarmed cancerous tissue is heated to a temperature of 50° C. to 55° C., and the temperature is maintained for 5 to 15 minutes during the heat treatment.

* * * * *